Figure 1:
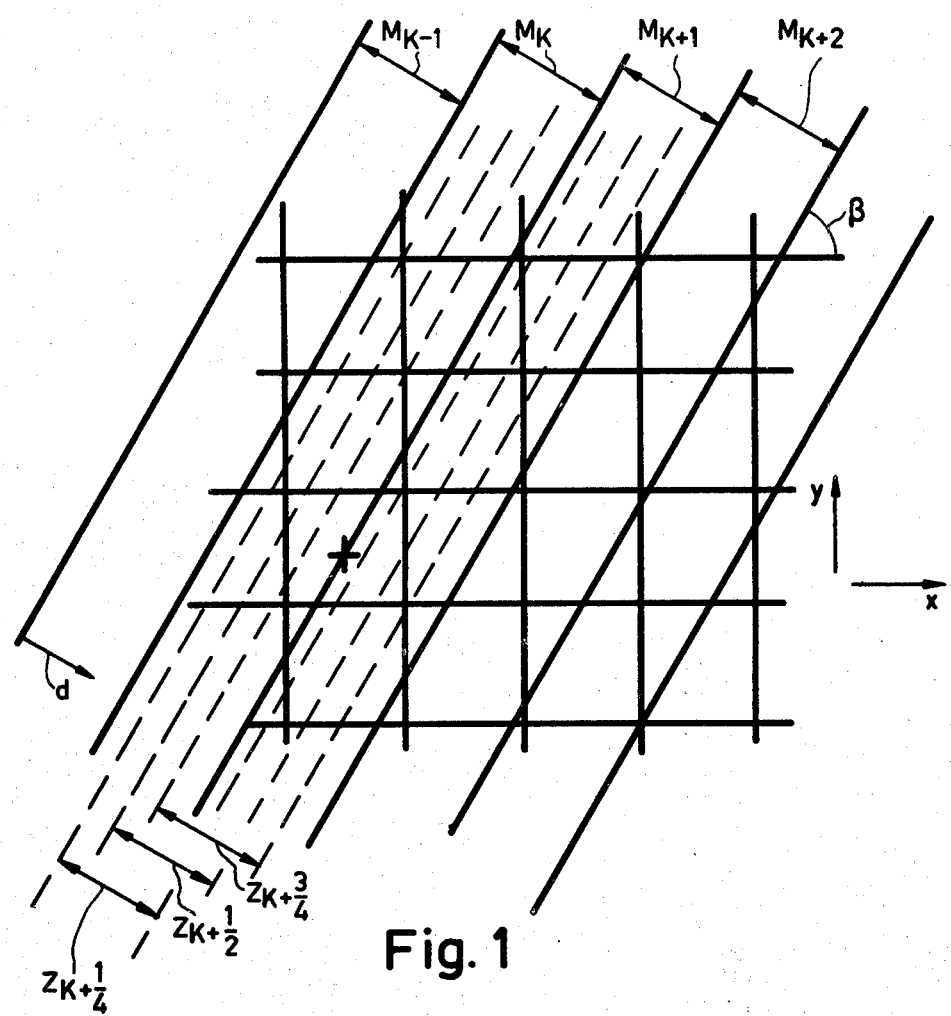

United States Patent [19]

Wagner

[11] 4,144,570
[45] Mar. 13, 1979

[54] METHOD OF AND DEVICE FOR MEASURING THE DISTRIBUTION OF A RADIATION IN A PLANE OF A BODY

[75] Inventor: Wolfgang Wagner, Norderstedt, Fed. Rep. of Germany

[73] Assignee: U.S. Philips Corporation, New York, N.Y.

[21] Appl. No.: 749,744

[22] Filed: Dec. 13, 1976

[30] Foreign Application Priority Data

Dec. 12, 1975 [DE] Fed. Rep. of Germany ....... 2556012

[51] Int. Cl.² ...................... G01N 23/06; G06F 15/42
[52] U.S. Cl. .................................. 364/414; 250/445 T
[58] Field of Search ................. 235/151.3; 250/445 T, 250/366, 369; 364/414

[56] References Cited

U.S. PATENT DOCUMENTS

| | | | |
|---|---|---|---|
| 3,778,614 | 12/1973 | Hounsfield | 250/445 T X |
| 3,784,820 | 1/1974 | Miraldi | 250/362 |
| 3,961,186 | 6/1976 | Leunbach | 250/445 T X |
| 3,971,948 | 7/1976 | Pfeiler | 250/445 T |
| 4,002,911 | 1/1977 | Hounsfield | 250/445 T X |
| 4,010,371 | 3/1977 | LeMay | 235/151.3 X |

Primary Examiner—Edward J. Wise
Attorney, Agent, or Firm—Thomas A. Briody; Jack E. Haken

[57] ABSTRACT

When reconstructing the absorption values at picture elements of a plane under examination from measured values which were measured by means of a scanner for transverse tomography, it is necessary to assign at least one intermediate value to each picture element from each measured series. In general said intermediate value must be computed from up to three measured values and weight factors. The invention describes a computation method in which the intermediate values which are assigned to the various picture elements are not computed accurately for the various picture elements but only to an approximation by interpolation. Computing time is, thus, substantially reduced with only a small increase in error.

11 Claims, 6 Drawing Figures

METHOD OF AND DEVICE FOR MEASURING THE DISTRIBUTION OF A RADIATION IN A PLANE OF A BODY

The invention relates to a method and device of measuring the distribution of the absorption or of the emission of radiation in a plane of a body divided into picture elements, of the type in which in a large number of measuring series the absorption and the emission, respectively, of the body are measured in a large number of directions situated in the plane and each measuring series provides a number of measured values of the absorption or of the emission along stripes extending at least approximately parallel with respect to each other, and in which intermediate values are formed from the measured values of a measuring series, which intermediate values are assigned to the picture elements situated in the plane and are added to the intermediate values previously assigned to said picture elements. Such a device is known from British Patent Specification No. 1,283,915. The absorption in a (human) body is measured by means of a radiation detector which, together with a radiation source generating the radiation on the other side of the body, is moved perpendicularly to the direction of the radiation. By means of the detector a series of measured values (measuring series) is measured which is a measure of the absorption of the radiation along straight lines through the body which extend parallel with respect to each other and are determined by the position of the source and the detector. After such a measuring series the source-detector system is rotated and a further measuring series are carried out at a different angles with respect to the body. The absorption in the plane cannot be reconstructed as such from the resulting measured values, because the measured values do not represent a measure of the absorption in various points but of the absorption along a straight line and a stripe, respectively, through the body to be examined. Mathematically this means that the value of a function has to be computed along a large number of intersecting straight lines in various points of the plane defined by the straight lines from the integrals of said function along a path through the body. A computing method for solving this problem is described in Proc. Nat. Acad. Sci. USA, Vol. 68, No. 9, pages 2236–2249, September 1971.

This problem is also present when measuring the radioactivity distribution in radio-actively marked biological objects, when computing layers of macromolecules (viruses and the like) which are measured by means of an electron microscope, and in the investigation of layers of technical objects (for example material test) by means of penetrating radiation.

In known devices the reconstruction of absorption is calculated by subdividing the examination plane into a matrix of quadratic picture elements whose dimension corresponds approximately to the width of a stripe. From each measuring series at least one measured value and a value derived therefrom, and from the other measured values of the measuring series, (for example by a convolution method) is assigned to each element (see German Offenlegungsschrift No. 24 17 317) along the stripe containing the picture element. Assuming that the picture element and the stripe have approximately the same widths, a picture element can be influenced by up to three measured values (and the values derived therefrom, respectively). In particular when the stripes extend obliquely with respect to the matrix, the measured values represent the absorption of the radiation along three juxtaposed parallel stripes so that interpolation between the measured values is necessary. In said interpolation for calculating the absorption of a picture element, the measured value and the value of a stripe derived therefrom, respectively, is multiplied by a weighting factor which corresponds to the common surface of the stripe containing the picture element.

When performed on a calculating machine, this method requires very long computing times and a very expensive calculating machine.

In order to obtain a shorter computing time with a simpler device it has been suggested (in German Offenlegungsschrift P 24 42 412, which corresponds to co-pending U.S. Pat. Application Ser. No. 685,271) to superimpose the measured values and the values derived therefrom, respectively, on the target of a charge storage tube along adjoining stripes whose position and direction corresponds to the position and direction of the stripes utilized in measuring the measuring values. However, signal-to-noise ratio problems arise with this technique.

It has furthermore been suggested (in German Offenlegungsschrift P 25 21 171.6) to divide each individual picture element into a number (for example 4 × 4) of picture sub-elements and to assign to each picture subelement the measured value of that stripe to each picture sub-element in which the center of the picture sub-element is situated. The absorption values of the various picture sub-elements of a picture element obtained in this manner are summed and the summed value is assigned to the picture element on the display apparatus. The number of picture sub-elements is thus larger (for example 16×) than in a method in which the width of a stripe corresponds to the dimensions of a picture element. As a result, the advantages obtained (from omission of the interpolations is partially offset.

It is the object of the invention to provide a simpler and less time-consuming method for measuring the absorption values of picture elements, and a device for carrying out the method. For that purpose, the method according to the invention is characterized in that for each measured value a number of subvalues are formed from the measured values, which subvalues represent the absorption along substripes whose center lines are equally spaced, after which an intermediate value is assigned to each picture element which is equal to the subvalue which represents the absorption in a substripe whose center line has the smallest distance to the center of the picture element.

The expressions "stripes of the measured values" and "substripes of the subvalues" are to be understood herein to mean those stripes and substripes, respectively, along which the measured values and the subvalues, respectively, represent the absorption. A "subvalue" may be identical to a measured value.

Thus, according to the invention it is not the intermediate value which represents the absorption along a stripe whose center line extends exactly through the center of the picture element; which is assigned to a but rather an intermediate value which is equal to the subvalue which represents the absorption along a substripe whose center line is closest to the centre of the picture element. In principle this may result in reconstruction errors. However, these are negligible, when a sufficient number of subvalues are formed per measured value, said number being $\geq 2$. The invention has the advantage, however, that for the reconstruction of the absorption in the plane only N × t computing operations need be carried out per measuring series, N being the number of subvalues per measured value and t being the number of measured values of a measuring series. When the width of the stripe corresponds approximately to the dimensions of the picture element, the number of measured values t corresponds approximately to the number of picture elements of the examination plane in the direction of the columns or rows. In the known method mentioned above, however, more than one interpolation often has to be carried out for each picture element. Thus $s^2$ interpolations have to be carried out, when s is the number of picture elements in the direction of the rows and columns. For a satisfactory resolving power, many picture elements have to be used, for example 180 picture elements per row and column; in this case, 180 × 180 interpolations would have to be carried out. In addition, the factors with which the measured values are weighted to form intermediate values may vary from picture element, to picture element in the known method, whereas in the method of the invention only three different weight factors are necessary when subvalues are formed by interpolation with three subvalues per measured value.

When the stripe width approximately corresponds to the dimensions of a picture element, a subvalue can be obtained by interpolation between measured values assigned to two juxtaposed stripes. The weight factor by which the measured values are multiplied depends on the distance between the substripe (centre line) of which the associated subvalue has to be determined and center of the lines stripes in which the two measured values used for the interpolation were measured. When the stripe width is constant for all the measured values, the same number of subvalues must be formed from two measured values. When the stripe width is not constant — for example, because the resolving power at the edge need not be so good as in the center — then the number of subvalues is proportional to the width of the stripes of the measured values from which they are formed. It is assumed hereinafter that the stripe width is the same for all the measured values.

When the width of a stripe in which a measured value is measured is considerably smaller than the dimensions of a picture element, the formation of a subvalue occurs by sampling summing, and integration of the measured values of several juxtaposed stripes, respectively, the sum of the stripe widths corresponding approximately to the dimensions of a picture element.

Figure 2:
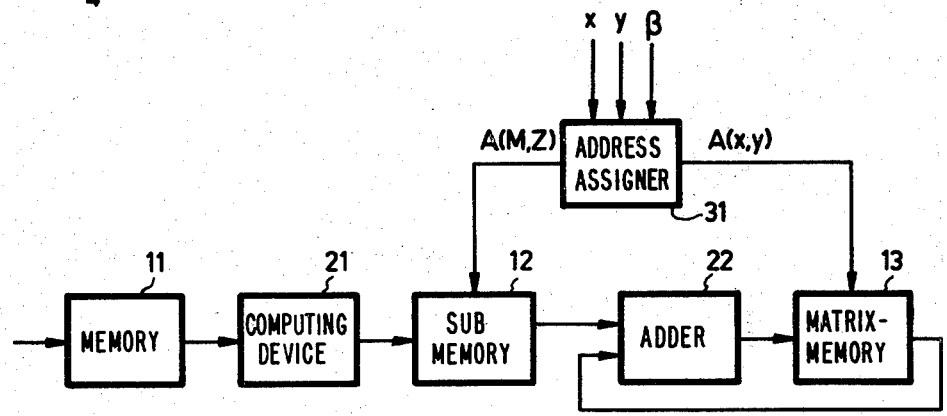
Figure 3:
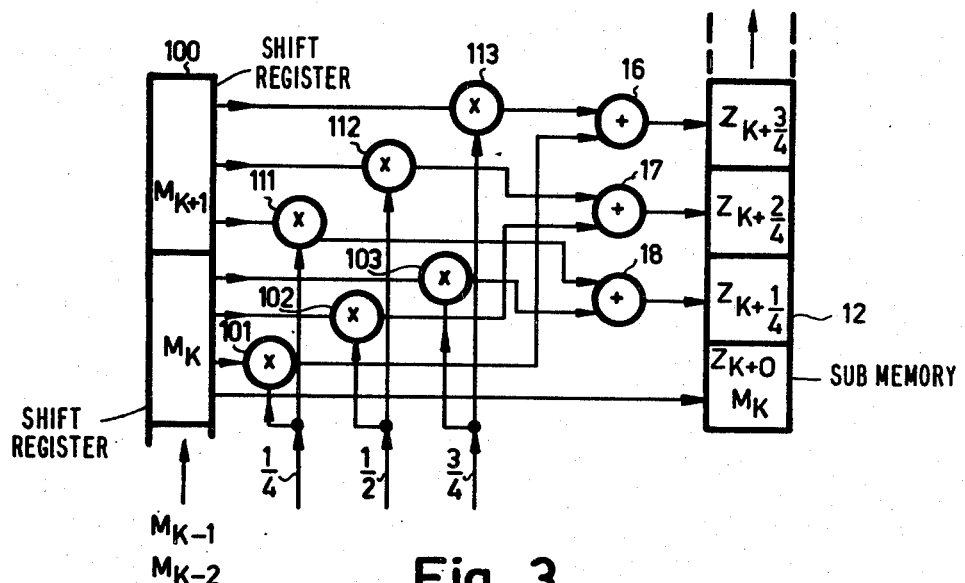
Figure 4:
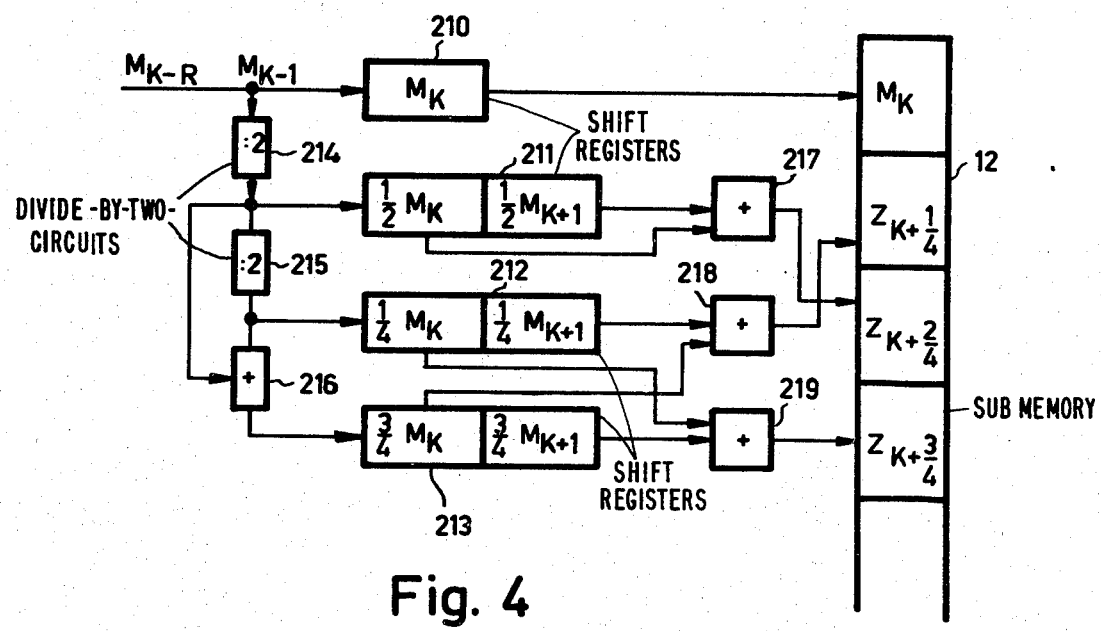
Figure 5:
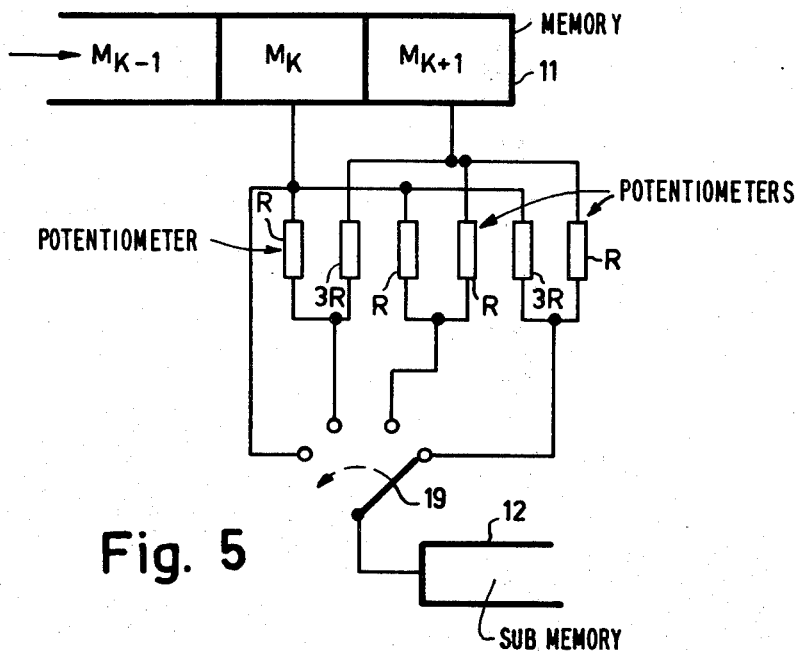
Figure 6:
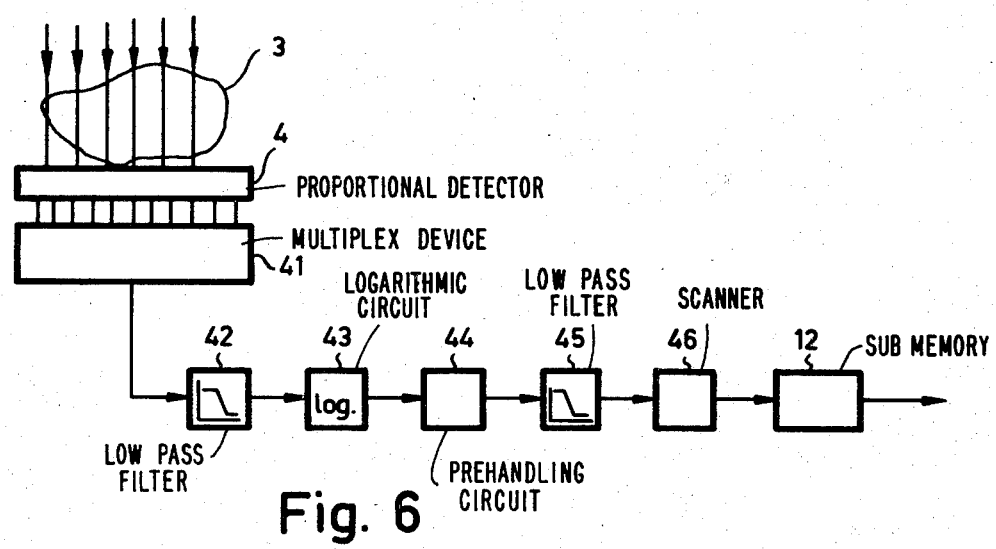

The invention will now be described in greater detail with reference to the accompanying drawings, in which FIG. 1 shows the position of the stripes with respect to a part of the picture elements of the plane of examination, FIG. 2 shows a first embodiment of a device for carrying out the method according to the invention, FIGS. 3 to 5 show various embodiments of a computing member necessary for the device for computing subvalues, and FIG. 6 shows another of a device for carrying out the method according to the invention.

FIG. 1 shows a few picture elements of the plane of examination which, in practice, may comprise, for example, 180 × 180 picture elements.

FIG. 1 further shows a few stripes intersecting the X-axis at an angle β along which the measured values $M_{k-1} \ldots M_{k+2}$ were measured in a measuring series. The width of such a stripe, which depends upon the dimensions of a radiation detector (not shown) and also on the width of the beam, corresponds to the dimensions of a picture element.

It may be seen from the drawing that it is not possible to assign to a picture element an intermediate value determined from only one measured value; for example, the center of the picture element marked by a cross, lies approximately at the boundary line (shown as a solid line) of the stripes for the measured values $M_k$ and $M_{k+1}$. In the known method mentioned above an intermediate value is therefore assigned to said picture element in which the measured values $M_k$ and $M_{k+1}$ are processed proportional to the inverse ratio of the distances of the center lines of their stripes to the center of the picture element.

The invention uses a simpler and faster way. Subvalues are interpolated from two measured values, $M_k$ and $M_{k+1}$ in accordance with the formula:

$$Z_k + \frac{n}{N} = M_k \cdot (1 - \frac{n+\delta}{N}) + \frac{n+\delta}{N} \cdot M_{k+1} \qquad (1)$$

in which:

N is an integer which is constant for all subvalues, n is also an integer which, however, may vary between 0 and N−1, $Z_k + n/N$ is the $n^{th}$ subvalue between the measured values and $0 \leq \delta < 1$, and is preferably equal to 0. A different interpolation formula may also be used, but formula (1) is a simple formula which is sufficiently accurate for this purpose. A subvalue denotes the absorption along the substripe whose center line is spaced at a distance which corresponds to the fraction (n+δ)N of the stripe width from the center line of the stripe of the measured value $M_k$ and which, is spaced from the center line of the stripe of the measured value $M_{k+1}$, by a distance which corresponds to the fraction 1− (n+δ)N of the stripe width.

In the drawing the stripes of the subvalues formed from the measured values $M_k$ and $M_{k+1}$ are shown as broken lines. Corresponding stripes also exist for the other measured values. Only four subvalues are shown in the drawing (in which δ=0, so that an intermediate value is formed from one measured value). The width of the substripe of a subvalue corresponds to that of a measured value. The center lines of the substripes of the subvalues lie at equal distances 1/N of the stripe width from each other.

An intermediate value is assigned to each picture element by selecting from all the subvalues that one subvalue which indicates the absorption along a stripe the center line of which is closest to the center of the picture element. For example, the intermediate value $Z_{k+\frac{1}{2}}$ is assigned to the picture element whose center is marked in the drawing by a cross, because the center of said picture element lies exactly on the center line of the substripe assigned to the corresponding subvalue. The center of the second picture element in the top row of picture elements on the contrary does not lie exactly on the center line of a substripe. Therefore that subvalue of the substripe whose center line is closest to said center is assigned to it: thus that is, an intermediate value $Z_{k+\frac{1}{2}}$. After an intermediate value has been assigned to each picture element in this manner of a measuring series, said process is repeated for the measured values of the next measuring series, in which the stripes intersect the plane of examination at a different angle β until the sum of all the intermediate values have been assigned to each picture element. The assignment of an intermediate value may be carried out by measuring the distance from a center of a picture element to a straight line which passes through the zero point of an x, y-system of co-ordinates, of which the x and y axes correspond to the direction of the rows and columns of the picture element matrix and which also intersects the x-axis at the angle $\beta$. An intermediate value is assigned which corresponds to a subvalue for which a center line of the associated substripe is spaced approximately the same distance from said straight line.

The distance from the center line of a substripe to the said straight line through the reference point has a linear relationship with the index of the subvalue (that is the distance determines which subvalue between two measured values of a measured series it is related to). The distance d from the centre of a picture element to the said straight line is given by the formula $$d = x \sin\beta + y \cdot \cos\beta \qquad (2)$$

where x and y are the position of the centre of the picture element in the x-y-system of co-ordinates.

FIG. 2 shows a circuit arrangement for carrying out the method according to the invention. The measured values of a measuring series (for a certain $\beta$) in the natural sequence ($\ldots M_{k-1}, M_k, M_{k+1} \ldots$) are stored in a memory 11. A computing device 21 calculates from the measured values (for example $M_k$ and $M_{k+1}$) of two juxtaposed stripes N subvalues according to the equation (1), when a number n is varied between 0 and N−1. These N subvalues are calculated successively for all measured values of a measuring series and stored in the submemory 12. The memory capacity of the submemory 12 must therefore be the N-fold of the memory capacity of the memory 11. The absorption values obtained for the various picture-elements with a center (x, y) are stored in the matrix-memory 13. The unit 31 ensures the assignment between a memory site of matrix-memory 13 and one from submemory 12 according to the equation $$N \times k + n = \text{INT} (N \times d + 0.5) \qquad (3)$$

INT is the rounding off to the next integer. For example, when the distance d from a center of a picture element to the straight line through the reference point = 3.27 (stripe widths), the operation N × d + 0,5 provides the value 13.58 (with N=4), the rounding off provides 13. Since N = 4, it follows that: k=3 and n=1, that is an intermediate value equal to the first subvalue between the third and fourth measured values is to be assigned to said picture element. The device 31 now ensures that the intermediate value to be assigned is read (in an interference-free manner) from the submemory 12 and is supplied to the one input of an adder circuit 22 at the other input of which the absorption value of the picture element to which the intermediate value is to be assigned is present. The absorption value of the picture element corresponds to the sum of the intermediate values which are assigned to the picture element from the preceding measuring series.

In this manner, each intermediate value derived from the measured values of a measuring series is assigned to each picture element. The method is then repeated for measured values of the next measuring series, the stripes extending at a different angle with respect to the plane.

The device 31 may in principle be a memory in which for each picture element (x, y) and for each measured series ($\beta$) the address A(x, y) of the picture element in the matrix-memory 13 and the address A(M, Z) of the memory site in the submemory 12 is stored which comprises the subvalue corresponding to the intermediate value to be assigned to said picture element. The addresses A(x, y) and A(M, Z) are fixed because they are not dependent on the measured values or the subvalues. Therefore, a very bulky address memory (disc or tape memory) would be necessary in each case.

Considerably less storage space is necessary when a computing member is used which calculates the distance d (according to formula (2)) and the values k and possibly n (according to formula (3)) from the co-ordinates x, y of the center of the picture element and from the angle $\beta$, and which forms, from the values x, y, the address A(x, y) of the memory site assigned to the picture element in matrix-memory 13, and the address A(M, Z) of the memory site in the submemory 12 in which the associated subvalue of index k + n/N is stored. A computing member which is suitable for these purposes and which determines the substripe for which the centre line to the center of the picture element has the smallest distance for each picture element and which assigns the subvalue of said substripe as an intermediate value to the picture element is described separately (in copending U.S. Pat. Ser. No. 685,271).

FIG. 3 shows an example of a computing device 21 for determing the subvalues in which N = 4 and $\delta$ = 0. A shift register 100 consisting of two register cells comprises in its two cells two measured values (for example $M_k$ and $M_{k+1}$) which were measured in a measuring series along juxtaposed stripes. The values $M_k$ and $M_{k+1}$ are each applied from the shift registers 100 to respective groups of multipliers wherein they are multiplied respectively by factors of $\frac{1}{4}$, $\frac{1}{2}$ and $\frac{3}{4}$. Thus $M_k$ and $M_{k+1}$ are multiplied by factors of $\frac{1}{4}$ in multipliers 101 and 111, respectively; factors of $\frac{1}{2}$ in multipliers 102 and 112 respectively and factors of $\frac{3}{4}$ in multipliers 103 and 113 respectively.

The outputs of the multipliers are then combined in adders 16, 17 and 18 to produce outputs in accordance with formula (1). Thus, the outputs of multipliers 101 and 113 are combined in adder 16 to yield a value equal to $\frac{1}{4} M_k + \frac{3}{4} M_{k+1}$; the outputs of multipliers 102 and 112 are combined in adder 17 to produce an output value of $\frac{1}{2} M_k + \frac{1}{2} M_{k+1}$; and the outputs of multipliers 103 and 111 are combined in adder 118 to produce a value $\frac{3}{4} M_k + \frac{1}{4} M_{k-1}$; the sum of the weighting factors always being equal to one. The subvalues thus obtained are stored in four successive memory cells of the submemory 12 together with the measured value $M_k$ which also serves as a subvalue. The measured value $M_k$ is then read in the memory cell provided previously for the measured value $M_{k+1}$, while the measured value $M_{k-1}$ is read in the memory cell previously occupied by $M_k$. At the same time the contents of the submemory 12 are shifted four memory sites so that the subvalues to be formed and the measured value $M_{k-1}$ can be read in the released memory site.

FIG. 4 shows another embodiment for the computing device 21 which is suitable for handling digital measured values and which because of a suitable choice of N(N=4) requires no multipliers.

A value $M_{k+1}$ is first present on the input line and is shifted simultaneously into the register 210 and the divide by-two 214. The binary coded measured value $M_{k+1}$ is divided by a factor of 2 in 214, which can be achieved by a simple shifting of the binary sites in a memory cell. The value $\frac{1}{2}M_{k+1}$ is then transferred in the shift register 211 and simultaneously in the divide-by-two 215 where it is divided again by the factor 2 (by shifting one binary site). The value $\frac{1}{4}M_{k+1}$ is then transferred into the shift register 212. The adder circuit 216 adds the values present at the outputs of divide-by-twos 214 and 215. The result $\frac{3}{4}M_{k+1}$ is transferred into the shift register 213. Thus, the values $M_{k+1}$, $\frac{1}{2}M_{k+1}$, $\frac{1}{4}M_{k+1}$ and $\frac{3}{4}M_{k+1}$ are present in the registers 210, 211, 212 and 213 of which register 210 has one memory cell and shift registers 211, 212 and 213 have two memory cells. The measured value $M_k$ is next applied to the input line. Corresponding fractional values are calculated from the measured value $M_k$ and transferred into the registers 210 to 213, the measured value $M_{k+1}$ and the values derived therefrom being shifted to the right. The measured value $M_k$ present at the output of the register 210 is then transferred into the submemory 12 as a subvalue. Simultaneously, adder 217 forms the sum of the contents of the two memory sites of the shift register 211, and the output signal thereof, which corresponds to the subvalue $Z_{k+\frac{1}{2}}$, is stored in the submemory 12. Adder 218 adds the contents of the second memory cell of the shift register 212 ($\frac{1}{4}M_{k+1}$) and the contents of the first memory cell of the shift register 213 ($\frac{3}{4}M_k$) and transfers the resulting subvalue ($Z_{k+\frac{1}{4}}$) into the submemory 12. Adder 219 adds the contents of the second memory cell of the shift register 213 ($\frac{3}{4}M_{k+1}$) and the contents of the first memory cell of the shift register 212. The resulting subvalues $Z_{k+\frac{3}{4}}$ is also stored in the submemory 12.

The content of the submemory 12 is then shifted four memory sites and the next computing cycle may start. The speed rate of the adders used in FIG. 4 may be comparatively slow as compared with the speed of the adder 22 (see FIG. 2), because for each $s^2$ (s is the number of picture elements in the x and y directions, respectively) additions which the adder 22 has to perform to process the subvalues present in the submemory 12, only approximately four times s-additions are preferred by the computing device 21 (s is normally coniderably larger than four and may be, for example, 180).

In the computing member according to FIG. 4 it is also feasible to use only one adder which performs the functions of the adders 216, 217, 218 and 219 cyclically.

FIG. 5 shows an embodiment of the computing device 21 in which it is assumed that the memory 11 and the submemory 12 analogously store the measured values and subvalues, respectively. CCD memories are, for example, suitable for this purpose. The outputs of two memory cells of the memory 11 in which measured values $M_k$ and $M_{k+1}$, which correspond to the absorption along adjacent parallel extending stripes of the plane of examination are stored are connected together via N (preferably four) potentiometers. The potentiometer ratio is $(N - m)/N$ wherein m is $0, 1, 2, \ldots N-1$ ($=3$). Voltage values which, are proportional to the subvalues can consequently be derived at potentiometer taps. A multiplex switch 19 connects the potentiometer taps and the output of at least one of the two memory cells successively to the input of the sub-memory 12.

In the embodiment shown in FIG. 1 it was assumed that the width of the stripe corresponds at least approximately to the dimensions of a picture element. The measured values of a measured series can be obtained as the source radiating through the object and its associated detector is shifted during the measured series, perpendicularly to the direction of the stripe, the width of a stripe. However, they can also be obtained by a series of juxtaposed detectors or detectors placed behind the body under examination. The stripes diverge thus from the measured values. By means of a special computing method (see, for example, German Patent Application P 25 11 231) values can be formed from said measured value which represent the absorption along parallel stripes. From the values which correspond to the previously described measured values, subvalues can be formed by the interpolation.

It is alternatively possible, however, to use a detector device which enables the measurement of the absorption of a body along stripes whose width is considerably smaller than the dimensions of a picture element in the plane of examination. For that purpose there may be used, for example, a proportional wire chamber in which a large number of wires are arranged beside each other distance which is considerably smaller than the dimensions of a picture element, or an X-ray radiation-sensitive fluorescent screen (for example of an image amplifier) having a television camera arranged behind it whose video signal is a measure of the absorption of the object.

Such a device with a wire chamber is shown in FIG. 6. Radiation passes through the object 3 from the source (in a manner not shown) and the radiation distribution behind the object is measured by the proportional wire chamber 4. The measured values of the proportional wire chamber 4 are scanned cyclically by a multiplex device 41 the output signal of which is supplied to the input of a low-pass filter 42 which eliminates the scanning noise. The output signal of the low-pass filter 42 is logarithmically amplified by a logarithmic circuit 43 and supplied to prehandling unit 44 which subjects the measured value to, for example, a convolution process. A low-pass filter 45 which has a lower limit frequency than the low-pass filter 42, is connected to the output of the prehandling unit 44. Specificly the upper limit frequency $f_o$ of filter 45 is chosen in accordance with the term $f_o = 1/NT$, where T is the time which the scanner 41 requires to scan a measured value assigned to a wire and N is the ratio between the width of a picture element and the distance between two wires.

Thus, the low-pass filter 45 integrates and sums the output signal of the scanner 41 over approximately N measured values so that the output signal of the low-pass filter 45 corresponds approximately to the signal which would be formed if the measured values were determined with detectors in which the effective measured surface corresponded to the dimensions of a picture element; thus the detectors would measure the absorption along stripes which correspond in width to the dimensions of a picture element.

The output signal of the low-pass filter 45 is sampled after each period T, subvalues being obtained which correspond to the absorption along substripes overlapping each other as is shown in FIG. 1. These subvalues are stored in the submemory 12, after which the further processing is carried out in the same manner as described with reference to FIG. 2.

Instead of a proportional wire chamber, a fluorescent screen or an image amplifier may be used which on its output screen shows a light intensity which is determined by the radiation distribution behind the object 3. This intensity variation is converted into a video signal by a television camera. The amplitude of the signal thus has a variation corresponding to the intensity of the radiation behind the object (dependent upon the place). The limit frequency of the low-pass filter 45 must correspond to the reciprocal value of that time T which the electron beam needs to scan the intensity along a track which corresponds to the distance between two picture elements. The scanning frequency of the scanner 46 is N times larger than the highest limit frequency of the low-pass filter 45, N being an integer $\geq 2$.

What is claimed is:

1. In a method for measuring the distribution of the absorption or of the emission of radiation in a plane of a body which is divided into picture elements, which method includes the steps of: measuring the absorption and the emission; respectively, in a large number of measuring series in a large number of directions in the plane, each measuring series providing a number of measured values of the absorption or of the emission along stripes extending at least approximately parallel with respect to each other; forming intermediate values from the measured values of a measuring series; assigning each of said intermediate values to one of said picture elements; and adding said intermediate values to intermediate values previously assigned to said picture element, the improvement wherein:

said forming step includes forming a number of subvalues from the measured values, which subvalues represent and absorption along substripes whose center lines are equally spaced; and said assigning step includes assigning an intermediate value to each picture element which is equal to the subvalue which represents the absorption in a substripe whose center line is closest to the center of the picture element.

2. A method as claimed in claim 1, wherein the distance between the center lines of two juxtaposed substripes is 1/N of the width of a stripe, N being an integer.

3. A method as claimed in claim 2, wherein N is equal to 4.

4. A method as claimed in claim 1, wherein the width of a stripe corresponds approximately to the dimensions of a picture element and the step of forming the subvalues includes interpolating the measured values.

5. A method as claimed in claim 4, wherein said interpolating step is performed in accordance with the equation $$Z_k + \frac{n}{N} = M_k (1 - \frac{n + \delta}{N} + \frac{n + \delta}{N}) M_{k+1}$$

in which $M_k$ and $M_{k+1}$, are the $k^{th}$ and $k+1^{st}$ measured value, respectively, N is the number of subvalues, n is an integer between 0 and N−1 and $Z_{k+n/N}$ is the $n^{th}$ subvalue between the $k^{th}$ and the $k+1^{st}$ measured value, wherein $0 \leq \delta \leq 1$.

6. A method as claimed in claim 1, wherein the width of each stripe is a fraction of the dimensions of the picture elements and the step of forming the subvalues includes sampling a signal formed by integration of a number of juxtaposed measured values.

7. A device for measuring the distribution of the absorption or of the emission of radiation in a plane of a body which is divided into picture elements, in which in a large number of measuring series the absorption and the emission, respectively, of the body are measured in a large number of directions in the plane, each measuring series providing a number of measured values of the absorption or of the emission along stripes extending at least approximately parallel with respect to each other, the width of each stripe corresponding approximately to the dimensions of a picture element, and in which intermediate values are formed from the measured values of a measuring series, which intermediate values are each assigned to one of said picture elements and are added to the intermediate values previously assigned to said picture element, including the improvement wherein, a number of subvalues are formed by interpolation of the measured values, which subvalues represent the absorption along substripes whose center lines are equally spaced, after which an intermediate value is assigned to each picture element which is equal to the subvalue which represents the absorption in a substripe whose center line is closest to the center of the picture element comprising:

a computing device connected for computing subvalues from the measured values by interpolation;

a submemory connected for storing the subvalues;

a matrix memory having a memory site for at least each picture element connected for storing the absorption values assigned to the various picture elements; and an assigning device which assigns to each picture element in the matrix memory an intermediate value which is equal to a subvalue stored in the submemory.

8. A device as claimed in claim 7, further comprising an adder circuit connected to the output of the submemory, one input of said adder being connected to the subvalue selected as an intermediate value assigned to a picture element and an other input of said adder being connected to the content of the memory site in the matrix memory assigned to that picture element; which adder circuit is further connected to store an output signal in said memory site after performing an addition.

9. A device as claimed in claim 7, wherein the computing member comprises a shift register having at least two memory cells, an output of each cell being connected to an input of each of three multiplier circuits, the other inputs of said multipliers being connected to constant factors smaller than one, and the output signals of pairs of the multipliers assigned to two different memory cells of the shift registers are supplied to the inputs of adder circuits.

10. A device as claimed in claim 7, wherein the computing device comprises:

a register connected for receiving digital measured values from an input line;

a first divide-by-two circuit connected recieve and half said measured values from said input line;

a second divide-by-two circuit connected to receive and half the output from said first divide-by-two circuit;

a first shift register, a second shift register, and a third shift register, each including two cells;

the cells of said first shift register being connected to receive, respectively, the outputs of said first divide-by-two circuit which are produced from two successive measured values;

a first adding circuit connected to sum the values from said cells of said first shift register, whereby a third subvalue is produced;

the cells of said second shift register being connected to receive, respectively, the outputs of said second divide-by-two circuit which are produced from said two successive measured values;

a second adding circuit connected to sum the outputs of said first divide-by-two circuit and said second divide-by-two circuit whereby adder output signals having a value equal to three quarters of said measured values are produced;

the cells of said third shift register being connected to receive, respectively, said adder output signals which are produced from said two successive measured values;

a third adding circuit connected to sum the value in said first cell of said third shift register with the value in said second cell of said second shift register whereby a second subvalue is produced;

a fourth adding circuit connected to sum the value in the first cell of said second shift register with the value in said second cell of said third shift register whereby a fourth subvalue is produced;

a first subvalue being obtained at the output of said register when the second of said successive measured values is stored therein.

11. A device as claimed in claim 7, wherein:

the memory comprises at least two cells, each adapted for storing an analog measured value, outputs of the cells being connected together via a plurality of potentiometers in each of which a potentiometer ratio on a divider tap satisfies a relation $(N-m)/N$, where N is the number of subvalues, $0 \leq m \leq N-1$; and a selection switch is connected for cyclically scanning the divider taps, one output of the selection switch being connected to an input of the submemory for storing subvalues formed on the divider taps of the potentiometers.

* * * * *